United States Patent [19]

Yamada et al.

[11] Patent Number: 4,624,770

[45] Date of Patent: Nov. 25, 1986

[54] AIR-FUEL RATIO SENSOR

[75] Inventors: Tetsusyo Yamada; Takao Kojima; Hiroyuki Ishiguro; Yutaka Nakayama, all of Nagoya, Japan

[73] Assignee: NGK Spark Plug Co., Ltd., Nagoya, Japan

[21] Appl. No.: 734,602

[22] Filed: May 16, 1985

[30] Foreign Application Priority Data

Jun. 26, 1984 [JP] Japan .................................. 59-130145
Jun. 26, 1984 [JP] Japan .................................. 59-130146

[51] Int. Cl.$^4$ ............................................. G01N 27/46
[52] U.S. Cl. .................................... 204/428; 204/426; 204/425
[58] Field of Search ......................... 204/1 S, 421–429

[56] References Cited

U.S. PATENT DOCUMENTS

| | | | |
|---|---|---|---|
| 4,159,234 | 6/1979 | Eifler et al. | 204/428 |
| 4,199,424 | 4/1980 | Teitelbaum | 204/428 |
| 4,247,380 | 1/1981 | McIntyre | 204/1 S |
| 4,505,807 | 3/1985 | Yamada | 204/428 |
| 4,507,192 | 3/1985 | Ebizawa et al. | 204/428 |

FOREIGN PATENT DOCUMENTS

| | | | |
|---|---|---|---|
| 2326086 | 12/1974 | Fed. Rep. of Germany | 204/428 |
| 0082762 | 5/1982 | Japan | 204/428 |

Primary Examiner—T. Tung
Attorney, Agent, or Firm—Fleit, Jacobson, Cohn & Price

[57] ABSTRACT

The air-fuel-ratio sensor has a mounting body, a cup-shaped protector enclosing a sensitive element, and gas passage holes and deflectors are provided on the protector wall in such a manner that a gas stream outside the sensor generates swirl of the gas in the cup-shaped protector, the amount of the swirling gas increasing with the distance from the mounting body.

10 Claims, 13 Drawing Figures

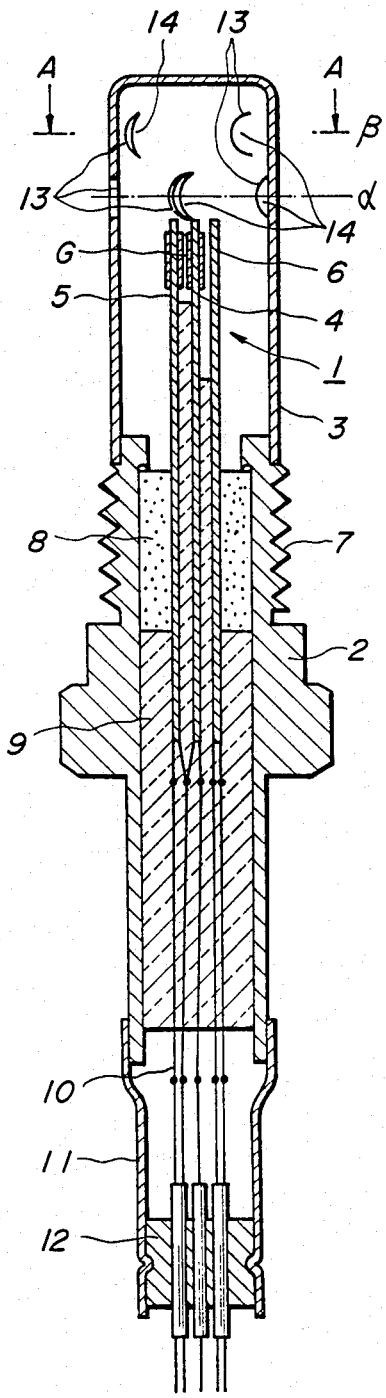
FIG_1A
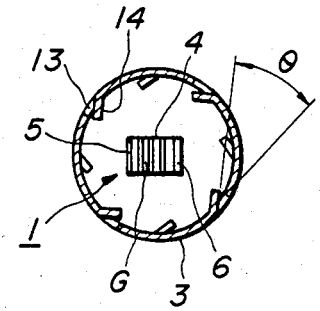
FIG_1B

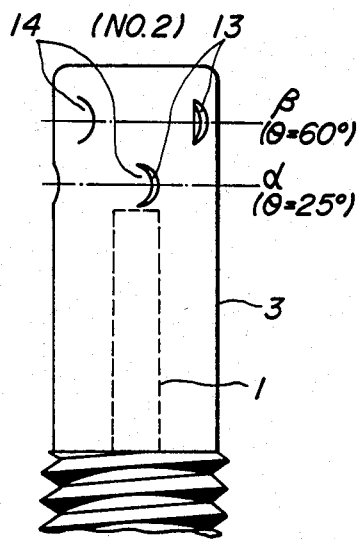
FIG_2A
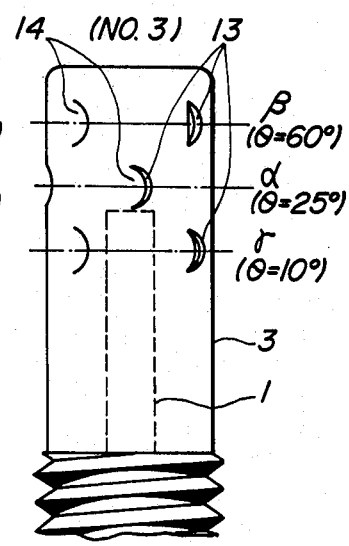
FIG_2B
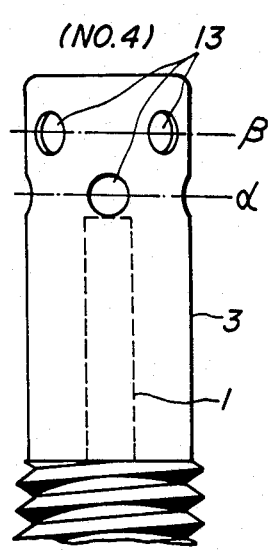
FIG_2C
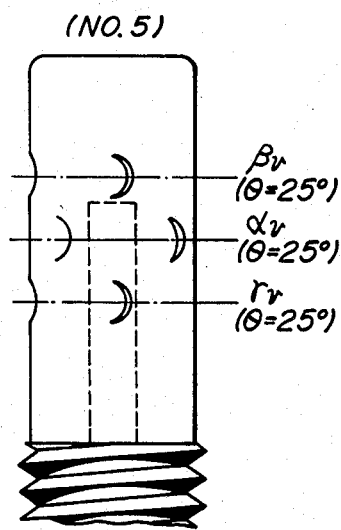
FIG_2D
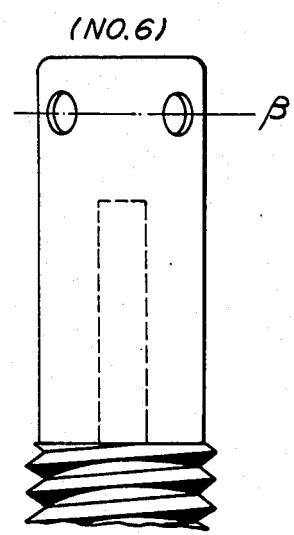
FIG_2E

AIR-FUEL RATIO SENSOR

BACKGROUND OF THE INVENTION

1. Field of the Invention

This invention relates to a gas sensor, and more particularly to an improvement of oxygen sensors which have been increasingly used as air-fuel-ratio sensors in streams of exhaust gas from internal combustion engines or the like. The invention is an outcome of research and development efforts for improving the response of an air-fuel-ratio sensor while eliminating detrimental cooling of the sensjtive element thereof by the stream of the gas being measured, and the air-fuel-ratio sensor of the invention can be applied, but not limited, to the control of fuel supply, liquid or gas, to combustion means such as automobile engines.

2. Description of the Prior Art

The applicants disclosed in their Japanese Patent Laying-open Publication No. 153,155/1983 an oxygen sensor comprising an oxygen pump element having an oxygen-ion-conductive solid electrolyte plate with a pair of aligned electrodes secured to the opposite surfaces thereof and an oxygen concentration cell element having an identical structure with that of the oxygen pump element, the two elements being disposed parallel to each other so that one electrode of the oxygen pump element faces one of the paired electrodes of the oxygen concentration cell element with a spacing therebetween, so as to define a diffusion-restricting narrow gap by such spacing.

With the oxygen sensor of the above structure, the oxygen pump element pumps out oxygen from the narrow gap to the outside of the oxygen sensor at a rate depending on the current through the two electrodes thereof. As the oxygen density in the narrow gap is reduced by such pumping, oxygen diffuses into the narrow gap from the outside at a rate depending on the diffusion resistance of the narrow gas and the difference of oxygen concentration between the inside and the outside of the narrow gap. When the inflow of oxygen toward the gap balances the oxygen extraction by the oxygen pump, the oxygen concentration in the narrow gap is stabilized. Thus, the oxygen concentration of the gas outside the oxygen sensor can be determined either by the voltage across the oxygen concentration cell element or the current through the oxygen pump element, and the response of such oxygen sensor can be made quick.

However, the above oxygen sensor has a shortcoming in that when it is disposed in a turbulent or agitated flow of the gas being measured, such as in an exhaust gas tube from an internal combustion engine, the performance of the oxygen sensor is considerably affected by such agitated stream of the gas.

To prevent such influence of the agitated stream of the gas being measured, it has been suggested to cover the sensitive element of the oxygen sensor by a porous cylindrical protector. The inventors have found that excessive cooling of the sensitive element by the gas stream is hardly prevented by a simple porous cylindrical protector. Especially, when a protector with a high porosity is used to improve the response characteristics, the detrimental excess cooling of the sensitive element has been inevitably enhanced.

SUMMARY OF THE INVENTION

Therefore, an object of the invention is to obviate the above-mentioned shortcoming of the prior art by providing an air-fuel-ratio sensor having an improved response characteristics without causing any excessive cooling of its sensitive element.

The inventors have noted that the following three points are particularly useful in fulfilling the above object of the invention.

(a) To avoid direct collision of the gas stream with the sensor unit by using a special structure of the protector.

(b) To bore holes on the wall of the protector in such direction that the gas entering through the holes generates a swirl or circulation of the gas around the sensor unit.

(c) To make the openings of the above holes large at those positions of the protector wall which do not face the sensor unit directly.

The above point (a) is effective in suppressing the excessive cooling of the sensor unit by the gas stream, the above point (b) is effective in improving the response of the sensor unit while suppressing the excessive cooling, and the point (c) is effective in improving the response.

BRIEF DESCRIPTION OF THE DRAWINGS

For a better understanding of the invention, reference is made to the accompanying drawings, in which:

FIG. 1A and FIG. 1B show a vertical sectional view and a horizontal sectional view of an air-fuel-ratio sensor according to the present invention;

FIG. 2A and FIG. 2B show two modifications of the hole arrangement on the wall of a cup-shaped protector according to the invention;

FIG. 2C through FIG. 2E show cup-shaped protectors which were tested by the inventors as Reference Specimens;

Figure 3:
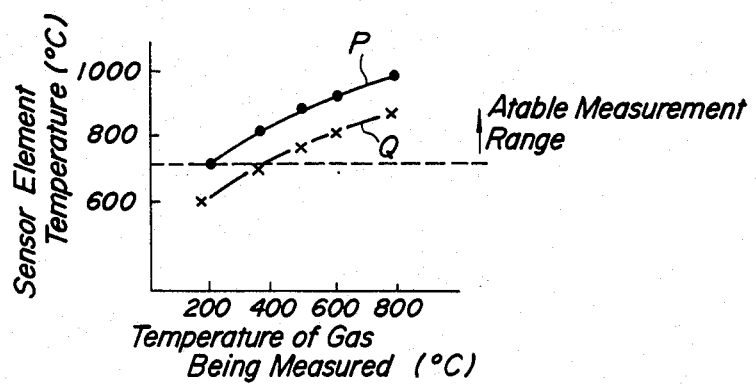
FIG. 3 is a graph showing the sensor unit temperature vs. the temperature of gas being measured characteristics for both a specimen of the invention and a reference specimen.

Throughout different views of the drawings, 1 is a sensor unit, 2 is a mounting body, 3 is a cup-shaped protector, 4 is an oxygen pump, 5 is an oxygen concentration cell, 6 is a heater, 7 shows mounting threads, 8 is filler, 9 is a glass seal, 10 is a lead wire, 11 is a conduit, 12 is a plug, 13 is a hole, 14 is a deflector, and G is a narrow gap.

DESCRIPTION OF THE PREFERRED EMBODIMENTS

Referring to FIG. 1, an air-fuel-ratio sensor of the invention comprises a sensor unit 1 extending above the top of a holding body 2 and a cup-shaped protector 3 having its open end secured to the top of the holding body 2 so as to surround the sensor unit 1 by the wall of the protector 3.

The sensor unit 1 has an oxygen pump 4 made of an oxygen-ion-conductive solid electrolyte plate carrying a pair of electrodes secured to opposite surfaces thereof and a wall means disposed in parallel to the solid electrolyte plate of the oxygen pump 4, so that a narrow gap G is defined between the wall means and one of the electrodes of the oxygen pump 4. The other electrode of the oxygen pump 4 is exposed to a gas being measured. The narrow gap G is a cavity with a diffusion-restricting function. In the illustrated embodiment, the wall means is an oxygen concentration cell 5 of the identical structure as that of the oxygen pump 4, and the narrow gap G is defined between one of the electrodes of the oxygen concentration cell and the facing electrode of the oxygen pump 4, as in the case of the above-mentioned oxygen sensor of the Japanese Patent Laying-open Publication No. 152,155/1983. The oxygen concentration cell 5 may be used to measure the ratio of oxygen concentration between the narrow gap G and the gas surrounding the sensor unit 1. Preferably, a heater 6 is disposed in the proximity of the oxygen pump 4 on the side opposite to the narrow gap G.

The mounting body 2 has mounting threads 7 formed on the outer surface contiguous to the top thereof, so as to facilitate its mounting on an exhaust gas tube or the like. The root end of the sensor unit 1, or its end opposite to the narrow gap G, is secured to the inside of the mounting body 2 by a layer of filler 8 and a glass seal 9. Preferably, the filler is a suitable heat-resistant inorganic adhesive, such as aluminium phosphate cement.

The solid electrolyte plate for the oxygen pump 4 and the oxygen concentration cell 5 may be made of stabilized zirconia. Each of the electrodes on opposite surfaces of the solid electrolyte plate may be in the form of a porous metallic film containing such metal oxide which has a finite resistance against oxygen diffusion. The electrode may be coated with a porous refractory material having a finite resistance against oxygen diffusion.

Lead wires 10 are connected to the root side end of the sensor unit 1 opposite to the end with the narrow gap G. The root end of the sensor unit 1 is buried in the glass seal 9 together with the lead wires 10. A conduit 11 is connected to the non-threaded end of the mounting body 2. The lead wires 10 are brought to the outside of the air-fuel-ratio sensor through a sealing plug 12 made of heat-resistant rubber, such as silicone rubber. The sealing plug 12 is fastened to the conduit 11 by pressing, so that the lead wires 10 are water tightly sealed by the plug 12.

Gas passage holes 13 are bored through the wall of the cup-shaped protector 3 having its open end secured to the top end of the mounting body 2 adjacent the mounting threads 7. The gas being measured outside the protector 3 enters therein through the holes 13 and comes in contact with the sensor unit 1.

The hole 13 is provided with a deflector 14. The disposition and shape of the holes 13 and the deflectors 14 are such that the gas entering into the protector 3 through the holes 13 generates a swirl or circulation. The amount of the swirling or circulating gas in the protector 3 increases with the distance from tip of the narrow gap G in the direction away from the mounting body 2.

The hole 13 and the deflector 14 can be formed simultaneously by the so-called press punching. The typical sidewall of the protector 3 is cylindrical, and the deflector 14 may be formed by inwardly bending or prying a portion of the sidewall. The opening which is left after such bending or prying of the sidewall acts as the hole 13. Referring to the A—A section of FIG. 1, the deflection angle $\theta$ of the deflector 14 is defined as the angle between that surface of the deflector 14 which faces the corresponding hole 13 and the tangential direction of the inner circumference of the protector 3 at the intersection of said surface of the deflector 14 with the inner circumference. It is important in this embodiment of the present invention that deflection angle $\theta$ for the deflectors 14 on a first row $\alpha$ of the holes 13 on a plane perpendicular to the longitudinal axis of the protector 3 intersecting the tip of narrow gap G of the sensor unit 1 must be smaller than that for the deflectors 14 on a second row $\beta$ parallel to the first row on the side away from the sensor unit 1.

When a third row $\gamma$ of the holes 13 and the deflectors 14 are formed in parallel to the first row on the side of the holding body 2 as shown in FIG. 2B, the deflection angle $\theta$ for the deflectors 14 on the third row must be smaller than that for the first row so that the amount of the swirling or circulating gas in the protector 3 increases with the distance from the mounting body 2.

The preferable magnitude of the deflection angle $\theta$ is 0–45 degrees for the first row $\alpha$ and 30–90 degrees for the second row $\beta$, provided that the deflection angle for the first row is smaller than that for the second row.

The inventors have found through tests that, when the protector 3 has an inner diameter of about 10 mm, the hole 13 can be in the form of a semicircle with a radius of about 2 mm with its chord in parallel to the longitudinal direction of the protector 3. About four of such holes 13 may be bored at uniform intervals on the first row $\alpha$, and about four to eight of uniformly spaced such holes 13 may be formed on the second row $\beta$. As far as the angular position relative to the longitudinal axis of the protector 3 is concerned, the holes 13 of the first row are preferably offset from those of the second row. In the above-mentioned tests, the sensor unit 1 had a width of about 4 mm, and the overall length of the protector 3 was about 20 mm, which length was about twice the projection of the sensor unit 1 above the top of the mounting body 2.

In operation, the air-fuel-ratio sensor is placed in an atmosphere of the gas being measured, and a negative potential is applied to the narrow gap side electrode of the oxygen pump 4 while a positive potential is applied to the opposite side electrode thereof. Whereby, oxygen ions travel through the solid electrolyte so as to extract or pump out the oxygen ions from the narrow gap G, and a difference of oxygen concentration is generated between the inside and the outside of the narrow gap G.

An electromotive force (EMF) is generated across the cell 5 due to the above difference of the oxygen concentration, and such EMF converges at a certain value when the diffusing inflow of oxygen ions to the narrow gap G through the three side openings thereof balances the above-mentioned oxygen extraction by the oxygen pump 4. Thus, when such balance is maintained by adjusting the current through the oxygen pump 4, the magnitude of the current to keep such balance of oxygen ion flow is substantially proportional to the oxygen concentration of the gas surrounding the sensor unit. Accordingly, the oxygen concentration of the surrounding gas can be determined by measuring the current of the oxygen pump 4 when such balance is achieved, provided that the sensor unit temperature is constant.

When the oxygen concentration cell 5 of FIG. 1 is replaced by a heat insulating refractory material plate without any electrodes so as to form the narrow gap G between such refractory material plate and the oxygen pump 4, a sufficiently high constant voltage is applied across the oxygen pump 4. Under such conditions, the current through the oxygen pump 4 represents the amount of oxygen extraction through the narrow gap G which amount depends on the oxygen concentration of the surrounding gas being measured. Accordingly, the oxygen concentration of the gas being measured can be determined by measuring the current of the oxygen pump 4, provided that the voltage applied thereto is constant and sufficiently high and that the sensor unit temperature is constant.

If the stream of the gas being measured, which stream enters into the protector 3 through the holes 13 thereof, is turbulent or highly agitated, the sensor unit 1 is apt to be excessively cooled by such agitated gas stream and the requirement of the constant temperature cannot be met. With the present invention, the above-mentioned disposition and the shape of the holes 13 and the deflectors 14 generate swirl or circulation of the gas within the protector 3, so that the risk of excessive cooling of the sensor unit 1 by agitated gas stream is completely eliminated. Thus, the invention contributes greatly to the improvement of the response characteristics of the air-fuel-ratio sensor.

The invention will be described in further detail by referring to examples.

EXAMPLE 1

Referring to FIG. 1, Specimen No. 1 of the invention was prepared by making a cup-shaped protector 3 having an inner diameter of 10 mm and a wall thickness of 0.3 mm, forming four semicircular holes 13 with deflectors 14, each hole having a radius of 2 mm on the sidewall of the protector 3 at uniform intervals so as to produce the first row $\alpha$, and forming four same semicircular holes 13 with deflectors 14 thereon so as to produce the second row $\beta$. The deflection angle $\theta$ of the deflectors 14 of the first row $\alpha$ was made 25 degrees.

Specimen No. 2 of the invention as shown in FIG. 2A was prepared in the same manner as the above Specimen No. 1 except that the deflection angle $\theta$ for only the deflectors 14 of the second row $\beta$ was made 60 degrees.

Specimen No. 3 of the invention as shown in FIG. 2B was prepared in the same manner as the above Specimen No. 2 except that a third row $\gamma$ of the holes 13 and the deflectors 14 was added on the cup-shaped protector 3 on the holding body 2 side of the first row $\alpha$. The deflection angle $\theta$ for the deflectors 14 of the third row $\gamma$ was 10 degrees.

Reference Specimen No. 4 as shown in FIG. 2C was prepared in a manner similar to the above Specimen No. 1 of the invention except that the holes 13 of the first and second rows $\alpha$ and $\beta$ were circular holes with a radius of 2 mm and no deflectors were provided.

Reference Specimen No. 5 as shown in FIG. 2D was prepared in a manner similar to the above Specimen No. 1 of the invention except that instead of the two rows $\alpha$ and $\beta$, three rows of similar holes 13 and the deflectors 14 were formed; namely, a row $\alpha_\nu$ on a plane perpendicular to the longitudinal axis of the cup-shaped protector 3 passing the narrow gap G of the sensor unit 1 and rows $\beta_\nu$ and $\gamma_\nu$ on opposite sides of the row $\alpha_\nu$. The deflection angle $\theta$ for all the deflectors 14 of this Specimen No. 5 was 25 degrees.

Reference Specimen No. 6 as shown in FIG. 2E was prepared in the same manner as that of the above Reference Specimen No. 4 except that only the row $\beta$ of circular holes 13 was formed and the row $\alpha$ was completely eliminated.

Tests were carried out on the Specimen thus prepared under the following conditions: namely, Test conditions Temperature measurement:

The surface temperature of the oxygen concentration cell 5 was measured by attaching a Chromel-Alumel thermocouple with a diameter of 0.32 mm on the electrode surface of the oxygen concentration sensor 5 and monitoring the thermoelectromotive force thereof.

Response:

Response time to a change of the ratio of excess air from 1.1 to 1.3 in the air-fuel-ratio of the intake air fuel mixture was measured, under the conditions that the Specimen sensor was mounted on the exhaust gas tube from a gasoline-injection engine with a replacement of 2,000 cubic centimeters, which engine was run so as to keep the average exhaust gas temperature at 450° C. and that a constant heater output 14 V.15 W was maintained. The result of the tests is shown in Table 1.

The "dispersion of indication" in Table 1, indicating the dispersion of the indication due to variation in the flow rate of the exhaust gas, was determined by comparing the sensor output for high-speed exhaust gas stream of about 3,000 liter/min corresponding to engine rotation of 3,000–4,000 rpm against the base sensor output for low-speed exhaust gas stream of about 600 liter/min corresponding to engine warm-up idling speed of 700–1,000 rpm.

TABLE 1

| | Specimen of Invention | | | Reference Specimen | | |
|---|---|---|---|---|---|---|
| Item | No. 1 (FIG. 1) | No. 2 (FIG. 2A) | No. 3 (FIG. 2B) | No. 4 (FIG. 2C) | No. 5 (FIG. 2D) | No. 6 (FIG. 2E) |
| Sensor unit temperature (°C.) | 900 | 880 | 850 | 800 | 750 | 930 |
| Response (mS) | 250 ± 50 | 200 ± 50 | 190 ± 50 | 200 ± 50 | 180 ± 50 | 350 ± 50 |
| Dispersion of A/F indication* | small | small | medium | fairly large | large | small |

*Dispersion in air-fuel-ratio (A/F) indication, 0–0.3 for "small", 0.3–0.5 for "medium", 0.5–1 for "fairly large", and more than 1 for "large".

As can be seen from Table 1, Reference Specimen No. 6 had a small dispersion of indication and a small temperature reduction, but its response was too slow. In the case of Reference Specimens No. 4 and No. 5, the response was improved to a practicable level, but their sensor units were cooled to below 800° C. and their dispersions of indication were too large for practical applications. On the other hand, Specimens No. 1 through No. 3 of the invention simultaneously achieved both the improved response and the elimination of excessive cooling of the sensor unit during operation.

FIG. 3 shows the sensor unit temperature vs. the temperature of gas being measured characteristics for the Specimens tested. The curve P of FIG. 3 is for Specimen No. 1 of the invention as shown in FIG. 1, while the curve Q of the figure is for Reference Specimen No. 5 as shown in FIG. 2D. The lower limit of the temperature range for stable measurement is shown by the dash line curve in FIG. 3. As can be seen from the figure, the temperature of the sensor unit 1 of Reference Specimen No. 5 becomes lower than the dash line curve for low-temperature gas being measured, and it cannot provide stable measurement for the gas whose temperature is below about 400° C. Thus, the measurable temperature range of Reference Specimen No. 5 is too narrow for practical applications.

EXAMPLE 2

Figure 5A:
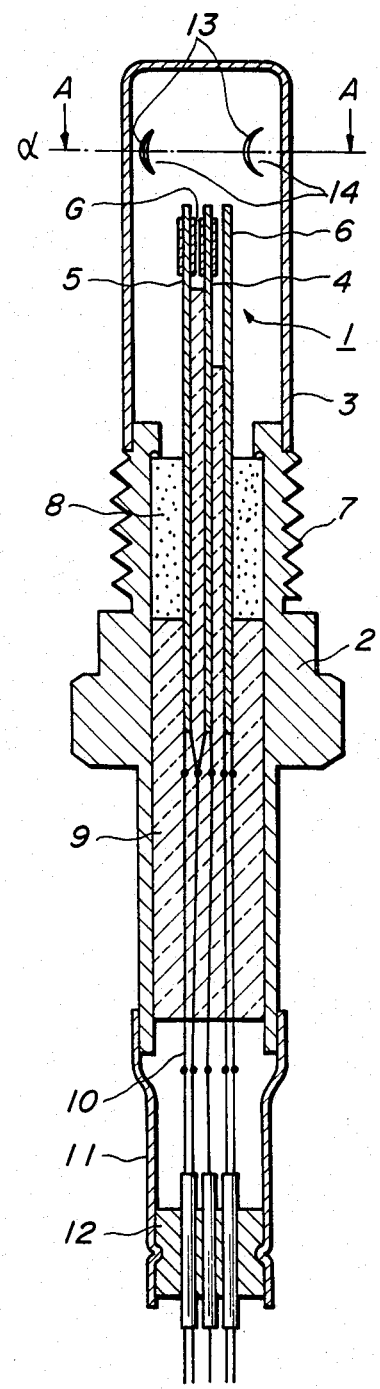
FIG. 5A and FIG. 5B show vertical sectional view and a horizontal sectional view of another embodiment of the air-fuel-ratio sensor of the invention.
Figure 5B:
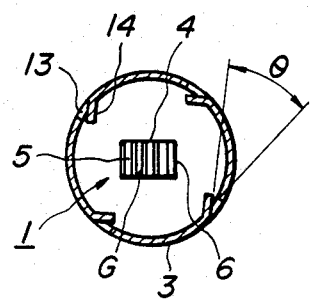

Referring to FIG. 5, Specimen No. 1A of the invention was prepared by making a cup-shaped protector 3 having an inner diameter of 10 mm and a wall thickness of 0.3 mm, and forming four semicircular holes 13 with deflectors 14, each hole having a radius of 2 mm on the sidewall of the protector 3 at uniform intervals. The holes 13 thus bored were on a plane perpendicular to the longitudinal axis of the cup-shaped protector 3 with a spacing from the sensor unit 1, so that the holes 13 were aligned in only one row $\alpha$. The deflection angle $\theta$ of the deflectors 14 of this Specimen 1A was 45 degrees.

The same tests as those of Example 1 were carried on the above Specimen No. 1A. The result is shown in Table 2 together with the test result on the Reference Specimens No. 4 through No. 6 of Example 1.

TABLE 2

| Item | Specimen No. 1A of Invention (FIG. 5) | Reference Specimen | | |
|---|---|---|---|---|
| | | No. 4 (FIG. 2C) | No. 5 (FIG. 2D) | No. 6 (FIG. 2E) |
| Senor unit temperature (°C.) | 920 | 800 | 750 | 930 |
| Response (mS) | 300 ± 50 | 200 ± 50 | 180 ± 50 | 350 ± 50 |
| Dispersion of A/F indication* | small | fairly large | large | small |

*Dispersion in air-fuel-ratio indication, 0–0.3 for "small", 0.5–1 for "fairly large", and more than 1 for "large".

As can be seen from Table 2, Specimen No. 1A of the invention simultaneously achieved both the improved response and the elimination of excessive cooling of the sensor unit during operation.

It was confirmed through tests that Specimen No. 1A of the invention had the sensor unit temperature vs. the temperature of gas being measured characteristics as shown by the curve P of FIG. 3.

Figure 4A:
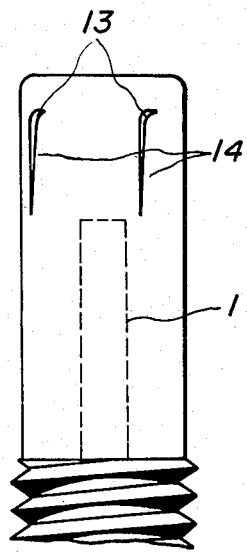
FIG. 4A, FIG. 4B, and FIG. 4C show modifications of the cup-shaped protector to be used in the air-fuel-ratio sensor of the invention.
Figure 4B:
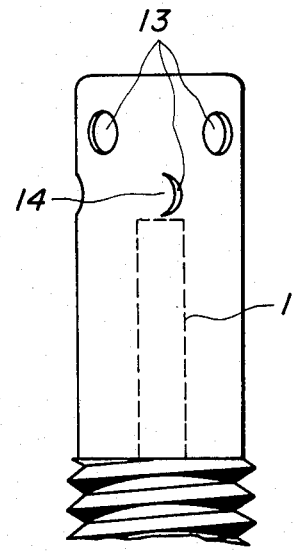
Figure 4C:
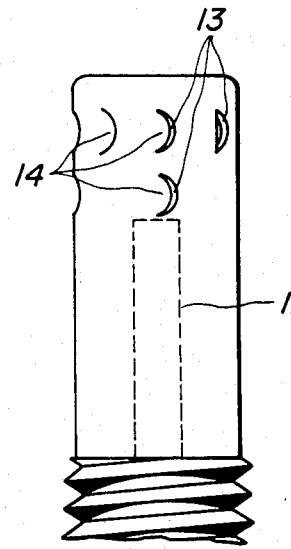

The shape of the gas passage hole 13 to be bored on the sidewall of the cup-shaped protector 3 for introducing the gas being measured into the protector 3 is not restricted to be semicircular or circular. For instance, the hole 13 can be an elongated slit as shown in FIG. 4A. The slit-shaped hole 13 of FIG. 4A extends between the rows $\alpha$ and $\beta$ of FIG. 1, and the width of the slit opening of such hole 13 increases as it extends away from the sensor unit 1 and the mounting body 2. A suitable deflector 14 is formed while punching such slit-like hole 13, so as to guide the gas flow into the protector 3. The holes 13 on the row $\beta$ of FIG. 1 can be made circular as shown in FIG. 4B. The number of the semicircular holes 13 with deflectors 14 on the row $\beta$ can be increased, for instance to eight, as shown in FIG. 4C. The inventors confirmed by tests that the modifications of FIG. 4A through FIG. 4C showed substantially the same performance as those of the above Specimens No. 1 through No. 3 of the invention.

As described in the foregoing, an air-fuel-ratio sensor of the invention has the special disposition and shape of gas passage holes 13 and deflectors 14 to be formed on the wall of a protector 3 surrounding a sensor unit 1, so that the air-fuel-ratio sensor of the invention has an improved response characteristics while eliminating adverse excess cooling of the sensor unit by highly agitated stream of the gas being measured.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. An air-fuel-ratio sensor, comprising a mounting body; a sensor unit extending away from a top of the mounting body and having an oxygen pump with a wall means formed at an extended tip of the sensor unit, said oxygen pump having an oxygen-ion-conductive solid electrolyte plate with a pair of electrodes secured to opposite surfaces thereof, said wall means facing one of said electrodes and being parallel thereto and spaced therefrom at a small spacing so as to define a diffusion-restricting narrow gap therebetween; and a cup-shaped protector having a closed end and a side wall, said protector being secured to said mounting body to enclose said sensor unit therein, said side wall of said cup-shaped protector having at least two rows of holes extending therethrough, said rows spaced axially along the longitudinal axis of said cup-shaped protector, and deflectors secured to the edges of the holes and extending inwardly of the protector at acute angles relative to the inner surface of the side wall of the protector, the angles of said deflectors in each row being greater than the angles of the deflectors in a preceding row in a direction along the longitudinal axis of said protector and toward said closed end, wherein said holes and said deflectors are such that gas outside the protector flows into the protector through said holes in a swirling motion, and the amount of said swirling gas in the protector increases with the axial distance from the mounting body.

2. An air-fuel-ratio sensor as set forth in claim 1, wherein said wall means is an oxygen concentration cell having an oxygen-ion-conductive solid electrolyte plate and a pair of electrodes secured to opposite surfaces of said solid electrolyte plate, one electrode of the oxygen concentration cell facing one electrode of said oxygen pump so as to define said narrow gap therebetween.

3. An air-fuel-ratio sensor as set forth in claim 1, wherein each of said holes is made by press punching the deflector at the edge thereof.

4. An air-fuel-ratio sensor as set forth in claim 1, wherein a row of said holes is on a plane perpendicular to the longitudinal axis of said cup-shaped protector, which plane is spaced away from said sensor unit with a small spacing from a tip of said narrow gap.

5. An air-fuel-ratio sensor as set forth in claim 1, wherein said holes are on two rows consisting of a first row on a plane perpendicular to the longitudinal axis of said cup-shaped protector, which plane passes the proximity of the tip of said narrow gap, and a second row parallel to the first row but farther away from said sensor unit than said first row, the holes of said first row being offset from the holes of said second row relative to said longitudinal axis of the cup-shaped protector.

6. An air-fuel-ratio sensor as set forth in claim 5, wherein a deflection angle of said deflector on said first row relative to the circumference of said cup-shaped protector is smaller than a corresponding deflection angle of said deflector on said second row.

7. An air-fuel-ratio sensor as set forth in claim 1, wherein said holes are on two rows consisting of a first row on a plane perpendicular to the longitudinal axis of said cup-shaped protector, which plane passes the proximity of the tip of said narrow gap, and a second row parallel to the first row but farther away from said sensor unit than said first row, the holes of said first row being smaller in number than the holes of said second row.

8. An air-fuel-ratio sensor as set forth in claim 7, wherein the holes of said first row are offset from the holes of said second row relative to said longitudinal axis of the cup-shaped protector.

9. An air-fuel-ratio sensor as set forth in claim 7, wherein the holes of said first row are aligned with the holes of said second row relative to said longitudinal axis of the cup-shaped protector.

10. An air-fuel-ratio sensor as set forth in claim 1, wherein said holes are on three rows consisting of a first row on a plane perpendicular to the longitudinal axis of said cup-shaped protector, which plane passes the proximity of the tip of said narrow gap, a second row parallel to the first row but farther away from said sensor unit than said first row and a third row on a plane which is parallel to the first row and passes through said sensor unit, the holes of said first row being offset from the holes of said second and third rows relative to the longitudinal axis of the cup-shaped protector.

* * * * *